US006287792B1

(12) United States Patent
Pardridge et al.

(10) Patent No.: US 6,287,792 B1
(45) Date of Patent: Sep. 11, 2001

(54) DRUG DELIVERY OF ANTISENSE OLIGONUCLEOTIDES AND PEPTIDES TO TISSUES IN VIVO AND TO CELLS USING AVIDIN-BIOTIN TECHNOLOGY

(75) Inventors: William M. Pardridge, Pacific Palisades; Ruben J. Boado, Agoura Hills, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 07/716,062

(22) Filed: Jun. 17, 1991

(51) Int. Cl.⁷ .................................................. G01N 33/53
(52) U.S. Cl. ............................................................ 435/7.5
(58) Field of Search ................................ 436/532; 435/6, 435/7.5, 7.9; 424/85, 88; 530/387.1, 324, 350, 399; 536/23.1, 23.5

(56) References Cited

U.S. PATENT DOCUMENTS

| | | | |
|---|---|---|---|
| 4,676,980 | * | 6/1987 | Segal et al. ............................. 424/85 |
| 4,711,955 | | 12/1987 | Ward et al. ............................. 536/29 |
| 4,803,297 | | 2/1989 | Levenson et al. ..................... 560/159 |
| 4,839,293 | * | 6/1989 | Cantor et al. ....................... 435/320.1 |
| 5,026,785 | * | 6/1991 | Mage et al. ......................... 525/329.4 |
| 5,122,453 | * | 6/1992 | Martin et al. ........................ 435/7.24 |
| 5,168,049 | * | 12/1992 | Meade et al. ......................... 435/69.1 |
| 5,169,933 | * | 12/1992 | Anderson et al. ................. 530/391.3 |

OTHER PUBLICATIONS

Bayer, E. et al., *Methods in Enzymology*, 184:138–160, 1990.*
Wilchek, M. et al., *Methods in Enzymology*, 184:5–13, 1990.*
Green, N. M., *Methods in Enzymology*, 184:51–67, 1990.*
Receptor–Mediated Gene Delivery and Expression in Vivo, by G.Y. Wu, et al., The Journal of Biological Chemistry, Oct. 15, 1988, vol. 263, No. 29, pp. 14621–14624.
Transferrin–Polycation Conjugates as Carriers for DNA Uptake into Cells, By E.Wagner, et al., Proc.Natl.Acad.Sci.USA, May 1990, vol.87, pp. 3410–3414.
Dissiociation of Avidin–Biotin Complex in Vivo, by R.D. Wei, et al., Experientia, 1970, vol. 27, pp. 366–368.
A Chemically Cleavable Biotinylated Nucleotide: Usefulness in the Recovery of Protein–DNA Complexes from Avidin.
Affinity Columns, By M.Shimkus, et al., Proc.Natl.Acad.Sci. USA, May 1985, vol. 82, pp. 2593–2597.
Biotin Binding to Avidin, by Y.Hiller, et al., Biochem,J., 1987, vol. 248, pp. 167–171.
Investigations of Avidin and Biotin for Imaging Applications, by D.J. Hnatowich, et al., The Journal of Nuclear Medicine, Aug. 1987, vol. 28, No. 8, pp. 1294–1302.
Biotination of Proteins in Vivo, by J.E. Cronan, Jr., The Journal of Biological Chemistry, Jun. 25, 1990, vol. 265, No. 18, pp. 10327–10333.
Rapid Blood Clearance of Biotinylated IgG After Infusion of Avidin, by V.V. Sinitsyn, et al., The Journal of Nuclear Medicine, Jan. 1989, vol. 30, No. 1, pp. 66–69.

* cited by examiner

*Primary Examiner*—Marianne P. Allen
(74) *Attorney, Agent, or Firm*—Shapiro, Borenstein & Dupont LLP (57) ABSTRACT

A composition for delivering an agent to cells in vitro or to tissues or organs in vivo. The composition comprises either avidin or an avidin fusion protein bonded to a biotinylated agent to form an avidin-biotin-agent complex. A method is further provided for delivering an agent to cells using the avidin-biotin-agent complex which involves administering the complex to an individual subject. The avidin-biotin-agent complex is used in therapeutic and diagnostic methods.

4 Claims, 3 Drawing Sheets

DRUG DELIVERY OF ANTISENSE OLIGONUCLEOTIDES AND PEPTIDES TO TISSUES IN VIVO AND TO CELLS USING AVIDIN-BIOTIN TECHNOLOGY

This invention was made with Government support under Grant No. AI-28760, awarded by the National Institutes of Health. The Government has certain rights in this invention.

BACKGROUND OF THE INVENTION

1. Field of the Invention

This invention relates to transport vectors for targeting drugs to cells in vitro and to tissues in vivo. In particular, this invention relates to targeting vectors based on avidin-biotin technology for delivery of peptides and oligonucleotides to cells and tissues in vivo and in vitro. The invention further concerns soluble transport vectors that are comprised of avidin fusion proteins which mediate cellular uptake of biotinylated oligonucleotides and peptides, as well as avidin protection of circulating oligonucleotides from serum 3'-exonucleases.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

Antisense oligonucleotides are potentially highly specific chemotherapeutic agents for the treatment of cancer, viral infections, and other disorders (1). There are two principal obstacles to effective delivery of antisense oligonucleotides to tissues: (a) poor transport of oligonucleotides across cell membranes, and (b) rapid degradation by tissue and serum nucleases. The minimal cellular uptake of the highly charged oligonucleotide compounds has been dealt with by adding to cells in tissue culture concentrations of antisense oligonucleotides ranging from 10 to 100 $\mu$M to achieve biological effects (3). Prohibitively higher concentrations will be required in vivo where capillary barriers retard the delivery of oligonucleotides to cells.

The nuclease problem has been dealt with by synthetic preparations of phosphorothioate nucleic acid derivatives (4). However, these nucleic acids require the use of unnatural nucleotides and thus cannot be prepared by recombinant DNA technology. The necessity for organic synthesis of the phosphorothioate oligonucleotide may significantly limit the industrial scale production of such compounds.

Liposomes have been used to deliver antisense oligonucleotides to tissues in vitro, in particular where capillary barriers are absent (5). However, liposomes are not effective delivery vehicles in vivo because they selectively deliver the drug to macrophages lining the reticuloendothelial system, and because they are too large to effectively cross capillary barriers in vivo (6). In particular, liposomes have not proven to be effective drug delivery vehicles for transport into brain across the brain capillary barrier system, i.e., the blood brain barrier (BBB) (7).

Recognizing this problem, other investigators have prepared polylysine conjugates with vector proteins such as asialofetuin, which is taken up by receptor mediated endocytosis into liver cells, or transferrin, which is taken up by organs expressing high quantities of transferrin receptor on the cell membrane (8, 9). The limitations of this approach are two-fold.

First, the asialofetuin- or transferrin-polylysine conjugate must be prepared chemically, oftentimes with low yields. Secondly, the interaction between the polylysine and the antisense oligonucleotide is not covalent and subject to rapid dissociation in vivo. Therefore, it would be advantageous to conjugate the antisense oligonucleotide to the transport vector via a high affinity bond that is stable in circulation but is labile in tissues.

It would be desirable to eliminate the need to couple the DNA binding protein to a vector compound. It would also be desirable if the targeting molecule to which the nucleotide binds would be stable in the circulation in vivo. It would be further desirable if such a targeted oligonucleotide was resistant to serum nucleases, thereby avoiding the need to use synthetic and unnatural oligonucleotides in preparation of antisense derivatives.

Current peptide delivery to tissues entails the use of liposomes (10), which have the limitation described above, and the preparation of chimeric peptides (11). The latter involves covalent conjugation, generally using disulfide bonds, of the pharmaceutical peptide to its transport vector.

This often involves complex linker chemistry. It would be desirable if peptide drug delivery could be achieved with simpler linker chemistry to yield linkage of a peptide to a transport vector, the linkage being of high affinity and in high yield. It would be further desirable if the link between the peptide and transport vector would be stable in plasma and labile in cells.

Peptide delivery to tissues in vivo involves the formation of chimeric peptides by covalent bonding of peptides to transport vectors. (11) The complex linker chemistry involved in the formation of chimeric peptides often produces low chemical yields which may not be optimal for industrial-scale production. It would be desirable to have linker chemistry in peptide delivery that is simple, associated with high yields and may be applied to industrial-scale production.

Accordingly, further developments are needed to make available a conjugation chemistry that would allow for tight binding of a drug, such as an oligonucleotide or peptide, to a transport vector within the circulation. It would be desirable to eliminate linker chemistry that involves covalent attachment of oligonucleotide or peptide drug to a tissue specific transport vector (12). Further desired would be a linker technology for drug delivery which provides the advantages of stability in plasma, lability in tissues, and high efficiency of drug/vector coupling that is necessary for industrial-scale production of chimeric peptides or oligonucleotides.

SUMMARY OF THE INVENTION

In accordance with the present invention, a composition is provided for delivering an agent to cells in vitro, or to cells within tissues or organs in vivo. The composition comprises either avidin or an avidin fusion protein as a transport vector bonded to a biotinylated agent to form an avidin-biotin-agent complex.

Further provided is a method for delivering an agent to cells using the composition of the present invention, which composition comprises the transport vector bonded to the biotinylated agent. The method includes contacting cells, in vivo or in vitro with the composition. The method involves administering the composition of the present invention to an individual subject for delivery of the agent to tissues and organs.

The present invention further provides a method for administering a therapeutic treatment to an individual which involves administering a therapeutic dosage to the subject of a pharmaceutical composition comprising the avidin-biotin-agent complex in a pharmaceutically-acceptable carrier.

A method is provided for administering a diagnostic treatment to a subject which involves administering to the subject an appropriate amount of the avidin-biotin-agent complex, wherein the agent is a diagnostic compound.

Further, a method is provided for synthesizing the avidin-biotin-agent complex. The method involves forming a transport vector, forming a biotinylated agent, and bonding the transport vector to the biotinylated agent via an avidin-biotin linkage to form an avidin-biotin-agent complex.

As pointed out above, the composition for delivering an agent to a cell comprises a transport vector bonded via an avidin-biotin linkage to a biotinylated agent to provide an avidin-biotin-agent complex. The transport vector includes an avidin moiety. The transport vector may further include a targeting moiety bound to the avidin moiety. The targeting moiety provides targeted transport of the avidin-biotin-agent complex to specific cells.

The present invention further envisions the transport vector as a substantially purified, fused polypeptide produced from a fused gene encoding nucleotide sequences encoding the avidin moiety and the targeting moiety. The invention further concerns itself with DNA sequences or DNA constructs, host cells, and recombinant methods for producing the fused polypeptide targeting vector.

The present invention provides useful advantages for delivery of antisense oligonucleotides to tissues in four respects. First, the cationic nature of avidin allows avidin to directly target cells, and eliminates the need to couple the cationic protein, such as polylysine to the targeting moiety, e.g., transferrin or asialo-glycoproteins by complex methods well known in the art (8, 9). Second, the high affinity nature of the avidin-biotin bond provides advantages of the present invention over well known methods for delivery of antisense oligonucleotides to tissues (8, 9) which rely on the low affinity interaction between the negative phosphate charges on nucleic acid molecules and the positive charges on the polylysine coupled to the transport vector. Third, the use of the avidin-biotin technology in the present invention eliminates the frequent need for complex methods of coupling between the polycationic protein (e.g., polylysine) and the transport vector (e.g., transferrin). The function of both of these proteins (i.e., transferrin and polylysine) are found together in the avidin molecule's cationic nature, which triggers absorptive-mediated endocytosis into cells, and in the avidin molecule's high affinity binding of biotin. Fourth, the 3' biotinylation of antisense oligonucleotides allows for avidin protection against 3' exonucleases in serum. This latter advantage is the basis for the method of the present invention which involves protecting oligonucleotides from 3' exonuclease degradation. By biotinylating an oligonucleotide toward the 3' end and reacting the biotinylated oligonucleotide with an avidin moiety, an avidin-biotin-oligonucleotide complex is formed which is resistant to 3' exonuclease degradation in serum.

The present invention also presents advantages in light of the well known methods of peptide delivery to tissues in vivo. Presently, peptide delivery involves the covalent coupling of peptides to their transport vectors in the formation of a chimeric peptide (16). The linker chemistry involved in the formation of chimeric peptides is usually complex and is at times associated with low chemical yield that may not be optimal for industrial scale production. Conversely, the chemistry of the present invention involved in biotinylation of peptides is simple, associated with high yields, and may be applied to industrial scale production.

The above discussed and many other features and attendant advantages of the present invention will become better understood by reference to the following detailed description of the invention.

BRIEF DESCRIPTION OF THE DRAWINGS

FIGS. 1a, 1b, and 1c refer to protecting oligonucleotides from exonuclease degradation by biotinylation of the oligonucleotide near the 3' end.

DETAILED DESCRIPTION OF THE INVENTION

The invention provides a composition for delivering an agent to cells, the composition including a transport vector bonded to a biotinylated agent through an avidin-biotin linkage to provide an avidin-biotin-agent complex.

The transport vector of the present invention is an avidin moiety by itself, or the avidin may be linked to a targeting moiety. The targeting moiety is useful for making the avidin-biotin agent complex more targetable, that is, better aimed than an avidin-biotin agent complex without a targeting moiety. By more targetable is meant that such targeting moieties have higher affinities for a more restricted range of tissues and organs. The targeting moieties of the present invention are selected from the group consisting of receptor ligands, such as but not restricted to insulin and transferrin, anti-receptor monoclonal antibodies, cationized proteins, and lectins.

The transport vector can be a fusion polypeptide comprised of an amino acid sequence for avidin (20) fused to an amino acid sequence representing a targeting moiety. The fusion polypeptides that make up the transport vector can be produced from a fused gene. Exemplary gene fusion systems for making the fusion polypeptides include a fusion gene sequence involving a construct between a DNA sequence encoding avidin and a DNA sequence encoding the constant and variable regions of an immunoglobulin. See FIG. 2. The gene structures encoding immunoglobulins are well known as are the methods for making fusion gene sequences or constructs between various portions of immunoglobulin genes and other genes. Employing these methods, the exons encoding the heavy chain genes, $C_{H2}$ and $C_{H3}$, are replaced by exons corresponding to the avidin gene. The avidin moiety is linked to the truncated immunoglobulin at the $F_c$ region. This fusion gene, along with genes encoding light chain variable and constant regions, may then be inserted in a variety of commonly used vector such as pPROK-1 (Clontech Laboratories, Palo Alto, Calif.) for a prokaryotic expression system or $pMAM_{neo}$ (Clontech Laboratories) or pSVL SV40 (Pharmacia, Piscataway, N.J.) for eukaryoitc expression systems. The fused gene has a nucleotide sequence encoding the fused polypeptide, and is comprised of a nucleotide sequence encoding the avidin moiety fused to a nucleotide sequence encoding the targeting moiety. Preferably, the nucleotide sequence that encodes the dimer subunit of avidin is used. A typical DNA sequence or construct encoding the fusion polypeptide of avidin and immunoglobulin variable region is schematized in FIG. 2, and incorporates sequences in reference no. 20 and in U.S. Pat. No. 4,839,293.

Figure 2:
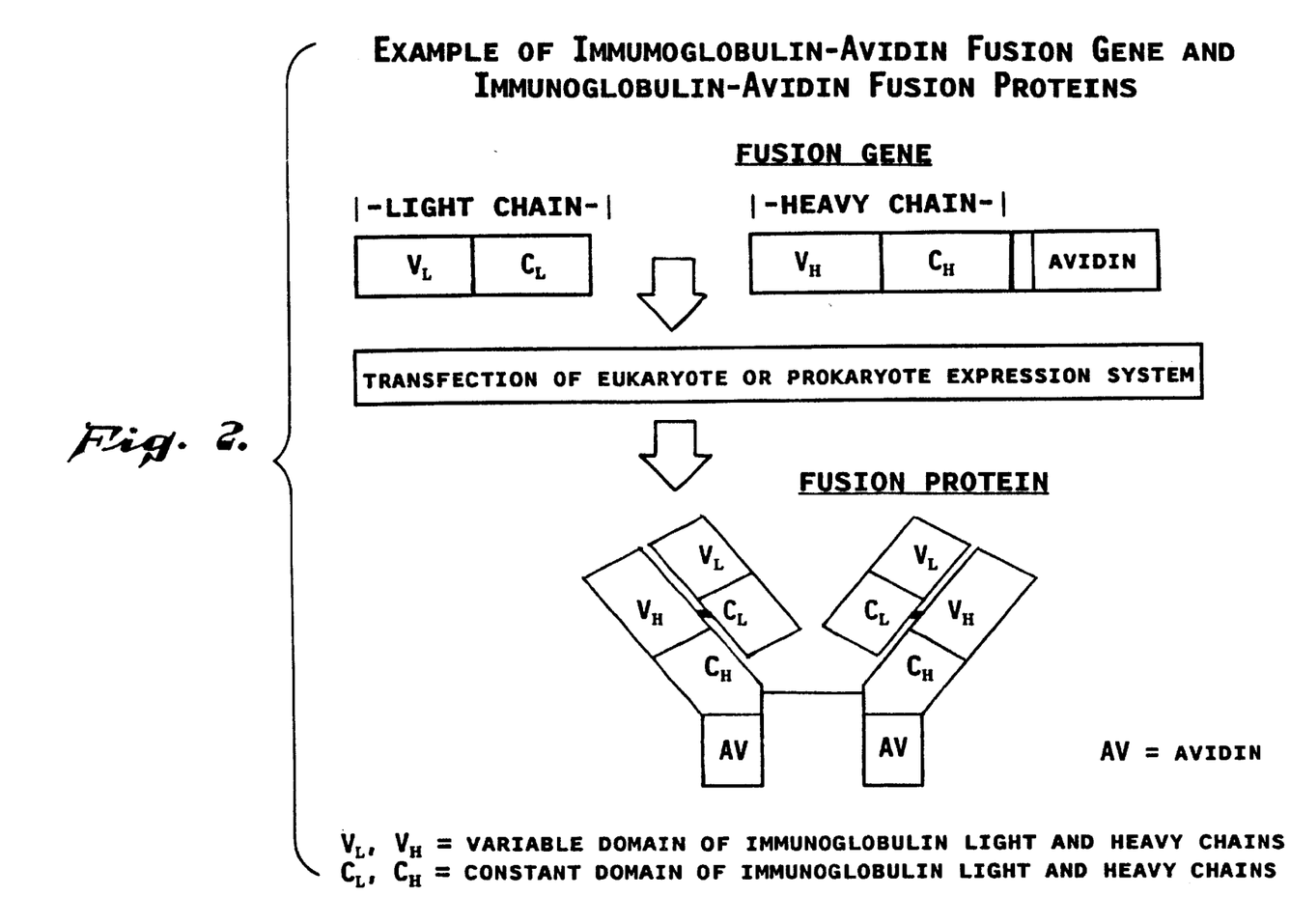
FIG. 2 is a diagram of an avidin fusion gene and avidin fusion protein of the present invention showing avidin linked to a tissue specific monoclonal antibody (immunoglobulin).

The present invention includes recombinant host cells containing DNA sequences, including those encoding the fusion polypeptide having the structure shown in FIG. 2. The recombinant host cell produces the fusion polypeptide in a sufficient quantity for a substantial isolation and purification of the fusion polypeptide. The fusion polypeptide itself is included in the present invention as well as compositions comprising the fusion polypeptide. Well known methods in the art are used for synthesizing recombinant fused proteins. (24) Typical recombinant host cells for producing the fusion polypeptide include eukaryotic cells, such as human embryonic kidney cells, and prokaryotic cells, such as E. coli.

Avidin is a cationic protein with an isoelectric point (pI) of 10, (13) owing to a preponderance of basic amino acids (lysine, arginine) relative to acidic amino acids (aspartic acid, glutamic acid) (13). In contrast, the bacterial homologue of avidin, called streptavidin, which is 38% homologous with avidin, is a slightly acidic protein with a pI of 5 to 6 (15). Like avidin, streptavidin binds biotin with extremely high affinity (15). Streptavidin, a bacterial protein, is not glycosylated, and is capable of functioning as the avidin moiety, binding biotin.

It has been shown that that avidin is taken up by tissues, such as brain, liver, and kidney by an absorptive-mediated endocytosis mechanism observed for other cationic proteins, such as histone or cationized albumin. (16, 17) This property of avidin can, if desired, eliminate the need for coupling avidin to a separate transport vector.

The protein avidin, as shown in the present invention, is a vector for the transportation to cells in vivo or in vitro of biotinylated agents, and has two features making it particularly suitable for drug delivery: (a) avidin is cationic, a property determined by the present inventors which allows avidin to undergo absorptive-mediated endocytosis into cells in vivo or in vitro, and absorptive-mediated transcytosis across microvascular barriers in vivo; and (b) avidin has a high affinity binding site for the water-soluble vitamin biotin. Biotin is a molecule that can be easily conjugated to oligonucleotides or peptides.

The avidin-biotin bond is one of the highest affinity binding reactions found in nature with a molar dissociation constant of $10^{-15}$M (13), and a t½ of ligand dissociation of 89 days (13). The avidin-biotin bond is stable in serum and in the circulation (18), but it is broken at the tissue site (18), where the drug may be released to produce pharmacological activity.

Avidin is a 64,000 dalton homotetramer glycoprotein (13), and has been administered to humans in large concentrations without untoward effects (19). Each 16,000 monomer of avidin contains a high-affinity binding site for the water-soluble vitamin biotin and the avidin tetramer binds four biotin molecules (13). The avidin gene cDNA has been cloned (20), and avidin can be produced in industrial-scale quantities using recombinant DNA technology.

The simple addition to avidin of biotinylated nucleic acids, or biotinylated peptide pharmaceuticals, results in the high affinity and direct action of the avidin moiety with the oligonucleotides or peptide pharmaceutical.

Biotinylated nucleic acids may be prepared chemically, by inserting an amino nucleotide at one end of the nucleic acid, or by recombinant DNA technology, employing a biotinylated nucleotide substrate. E. coli DNA polymerase recognizes biotinylated nucleotides (21). The avidin cDNA has been cloned (20), and the preparation of fusion proteins, wherein avidin is genetically fused to an organ-specific vector (see FIG. 2) may eliminate the rapid clearance of avidin from blood. This approach may also provide a strategy for industrial-scale production of avidin chimeric peptides that are suitable for delivery of biotinylated anti-sense oligonucleotides or peptides to tissues in vivo.

Peptides may be biotinylated chemically, using activated biotin analogues, such as N-hydroxysuccinimidobiotin (NHS-biotin), which is commercially available from Pierce Chemical Company, Rockford, Ill. and requires the presence of a free primary amino group on the peptide. Moreover, peptides and proteins produced by recombinant DNA technology may be biotinylated in industrial quantities by preparing fusion genes that encode for an approximately 75 amino acid consensus sequence that allows for biotinylation of a lysine residue by E. coli biotin ligase, which results in the bacterial secretion of biotinylated protein (22).

Therefore, biotinylated peptides and proteins, biotinylated oligonucleotides, and avidin may all be produced by recombinant DNA technology.

It should be noted that, although avidin is 10% glycosylated, the non-glycosylated avidin still binds biotin with equally high affinity (23). Therefore, non-glycosylated avidin produced in bacterial expression systems, in accordance with the present invention, is preferred for pharmaceutical purposes.

The avidin moiety of the present invention can be the monomer subunit of avidin, the dimer subunit, or the tetramer. Either the glycosylated- or non-glycosylated derivatives of the avidin monomer, dimer, or tetramer may be used. Use of the avidin oligomer is preferred because the affinity of the monomer for biotin is much less than the affinity for biotin of the oligomer (14). The biotinylated agent of the present invention is bonded to the avidin moiety of the transport vector via an avidin-biotin linkage. The molecule formed by this linkage is referred to in this description as an avidin-biotin-agent complex.

The invention concerns at least one biotinylated agent bonded through an avidin-biotin linkage to a transport vector. According to the present invention, the agent which is biotinylated according can be polybiotinylated. Preferably, the agent is monobiotinylated to avoid the formation of aggregates which might be insoluble or rapidly removed by liver function or by the reticuloendothelial system.

According to the present invention, an agent to be biotinylated for delivery to cells is selected from the group consisting of oligonucleotides, polypeptides, immunoglobulins, and organic chemicals. The biotinylated agents are preferably monobiotinylated and selected from the group consisting of agents considered above.

As described below in Example 3, the biotinylated agent moiety can be an oligonucleotide which is biotinylated at the 3' end of the oligonucleotide. This provides the advantage of preventing degradation of the biotinylated oligonucleotide in serum by 3' exonucleases. The oligonucleotide can be an antisense oligonucleotide. Typical antisense oligonucleotides which can be used in the composition of the present invention include those complementary to the mRNA corresponding to oncogene products, viral-specfic proteins, enzymes, transporter proteins, or other peptides and oligonucleotides vital to normal or pathologic cellular function.

According to the invention, a method is provided for protecting oligonucleotides from 3' exonuclease degradation in serum and from 3'exonuclease degradation in tissues where they may be present. (See Example 3, below) The method for protecting oligonucleotides from 3' exonuclease degradation involves the step of biotinylating the oligonucleotide to form a biotinylated oligonucleotide. The site of biotinylation is toward the 3' end of the oligonucleotide. The method reacts the biotinylated oligonucleotide with an avidin moiety to form an avidin-biotin-oligonucleotide complex, protecting the oligonucleotide from 3' exonuclease degradation upon administration to an individual or to cells in vitro where exonucleases may be present.

The agent which is biotinylated according to the method of the present invention can be a pharmaceutical compound selected from the group consisting of but not restricted to methotrexate, amphotericin, catecholamines, or peptides. Amphotericin is useful in treating brain fungal diseases, catecholamines useful for treating depression or Parkinson's disease.

Agents which are diagnostic compounds can be biotinylated for use in the invention. Such diagnostic compounds can be selected from the group consisting of, but not restricted to oligonucleotides, immunoglobulins, amyloid ligands, and receptor ligands. Receptor ligands which are biotinylated in the present invention are not restricted to peptides, catecholamines, or steroid hormones. Typical diagnostic procedures in which these compounds are employed include, but are not restricted to, search for tumors, amyloid, abcess, or auto-immune reactions. For example, amyloids are proteinaceous, gel-like deposits that are formed in disease processes, such as Alzheimer's Disease. Amyloids have a special binding affinity for certain proteins in the blood, such that when the protein comes in contact with the amyloid, the protein will stick to it. Those proteins can be tagged with radioactivity. When these tagged proteins bind to the amyloid, it is possible to image the pattern of binding and observe a condition such as Alzheimer's Disease.

In accordance with the present invention, a pharmaceutical composition is provided which includes the composition of the present invention in a pharmaceutically-acceptable carrier. Suitable pharmaceutical carriers are selected on the basis of the nature of the avidin moiety, the biotinylated agent comprising the avidin-biotin-agent complex, the presence of the targeting moiety linked to the transport vector, the targeted cells in vivo (issue/organ) or in vitro, and the particular use—therapeutic, diagnostic, or otherwise. For example, a suitable pharmaceutical carrier for the avidin-biotin-agent complex consisting of avidin-biotinylated oligonucleotide is normal saline, as illustrated in Example 1, below. Other suitable pharmaceutical carriers for particular uses are saline solutions containing dilute detergents.

The avidin-biotin-agent complex of the present invention is useful in delivery of the agent to cells. These cells are organs and tissues within an animal. A method for delivering an agent to organs and tissues within an animal involves the step of administering the avidin-biotin-agent complex to the subject. Further, the avidin-biotin-agent complex is useful for delivery of an agent to cells located in vitro. For example, cell cultures in dishes or flasks are delivery targets for the transport vector linked to the biotinylated agent according to the present invention. In the appropriate carrier, the avidin-biotin-agent complex is added to the medium in which cells are growing in vitro and thereby the invention achieves contacting those cells with the transport vector and the delivery of the avidin-biotin-agent complex to the cells. Appropriate carriers include normal saline or tissue culture medium.

The avidin-biotin-agent complexes in accordance with the present invention are well-suited for delivering an agent to cells both in vivo or in vitro. A first step of the method provides a composition which includes a transport vector linked to a biotinylated agent through an avidin-biotin linkage to provide an avidin-biotin agent complex. The transport vector linked to the biotinylated agent may further include a targeting moiety. The targeting moiety provides targeted transport of the avidin-biotin-agent complex to specific cells. The second step of the method is contacting the cells with this composition. The cells include tissues and organs in vivo and cells in vitro.

The method delivers an agent to tissues and organs in vivo such as the brain, liver, kidney, lung, or heart. A composition having the avidin-biotin-agent complex is administered to an individual in a pharmaceutically-acceptable carrier. Methods for administering the avidin-biotin-agent complex to individuals involve administering a therapeutic dosage to the subject. A therapeutic dosage can be from about 0.001 milligrams per kilogram to about 1 milligram per kilogram.

The invention further includes a method for administering a diagnostic treatment to a subject, which involves administering to the subject an appropriate amount of the avidin-biotin-agent complex. In this diagnostic complex, the agent can be a specific monoclonal antibody that is labeled with either an isotope or an appropriate contrast agent. Such treatments would be used for the purpose of diagnosing the presence of cancer, various autoimmune diseases, such as multiple sclerosis, or other conditions involving brain abscesses and neurodegenerative conditions, such as Alzheimer's disease.

According to the invention, the avidin-biotin-agent complex may be prepared in a number of different ways. The steps of the methods involve forming a transport vector, the transport vector having an avidin moiety selected from the group consisting of the avidin tetramer, the avidin dimer, and the avidin monomer subunit. Glycosylated and non-glycosylated derivatives of the avidin can be used in the present invention. Another step is to form a biotinylated agent. Avidin-biotin-agent complexes are formed by making a bond between the avidin of the transport vector and the biotin of the biotinylated agent to provide an avidin-biotin linkage and a stable avidin-biotin-agent complex. The transport vector can also include a targeting moiety bound to the avidin moiety. The transport vector can be synthesized by recombinant means, as well.

The following examples are offered by way of illustration and are not intended to limit the invention in any manner.

EXAMPLE 1

Avidin-Biotin Soluble Transport Vector

This example demonstrates that the avidin-biotin system of the present invention is capable of mediating specific cellular uptake of biotinylated antisense oligonucleotides or peptides to cells in vitro and tissues in vivo.

The model antisense oligonucleotides used in these studies was a 21-mer complementary to the bovine GLUT-1 glucose transporter mRNA (2) and corresponds to nucleotides −9 to +12 (where +1 corresponds to the first nucleotide of the methionine initiation codon) and the thymine base at +10 of the mRNA is replaced by 6-amino uracil suitable for biotinylation within NHS-biotin near the five prime end of the antisense oligonucleotide, (see Formula I, below).

Formula I

An extended primary amine group was added to the antisense oligonucleotide by replacing the deoxythymidine at position 3, with 6-aminodeoxyuridine (aU) (Genosys Biotechnologies, Inc., The Woodlands, Tex.), yielding the following oligonucleotide, 5'-GGaUGGGCTCCATGGCCGCGCT-3'. The oligonucleotide was biotinylated by adding 73 nmol of NHS-biotin (Pierce Chemical Co., Rockford, Ill.) to 6.9 nmol of amino-modified antisense oligonucleotide in 0.125 M NaHCO$_3$ at pH=9. Following biotinylation, the product was purified by Sephadex G-25 gel filtration and labeled at the 5' end with polynucleotide T$_4$ kinase using [γ-P$^{32}$]-ATP, and this labeling resulted in a final product with a specific activity of 2.6 microcuries/pmol. The labeled oligonucleotide was repurified through a Sephadex G25 column, avidin was added, and the avidin-biotin DNA complex was purified by Sephadex G75 column chromatography prior to all experiments.

The model peptide employed in this study was [desamino-Cys$^1$, D-Lys$^8$] lysine vasopressin (DDLVP). Both in vitro and in vivo delivery of biotinylated DDLVP and biotinylated GLUT-1 antisense oligonucleotide were achieved.

Two different types of biotin analogues were employed in these studies. The GLUT-1 antisense oligonucleotide was biotinylated with N-hydroxysuccinimidobiotin (NHS-biotin), [P$^{32}$]-labeled at the five prime end to form [P$^{32}$] bio-DNA. The NHS-biotin was obtained from Pierce Chemical Company, Rockford, Ill. This biotinylation reaction resulted in the formation of an avidin-biotin bond that was resistant to thiol cleavage. The DDLVP was iodinated and then biotinylated with a cleavable biotin linker employing sulfosuccinimidyl-2-(biotinamido)ethyl-1, 3-dithiopropionate (NHS-SS-biotin) to form [I$^{125}$]-bio-SS-DDLVP. This resulted in the formation of a disulfide-based linker and allows for thiol-based cleavage of the biotinylated drug from the avidin vector (21).

The DDLVP was synthesized by Peninsula Laboratories in Belmont, Calif. and was purified to homogeneity by C18 reverse phase high performance liquid chromatography and was radio labeled with I$^{125}$ iodine and chloramine T, followed by purification through a C18 Sep Pak extraction cartridge. A ten-fold molar excess of NHS-SS-biotin (Pierce Chemical Co., Rockford, Ill.) was added to 10 nmol of I$^{125}$-DDLVP and 2 ml of 0.125 M NaHCO$_3$ (pH=9), and following biotinylation, the excess reagents were removed as follows: 1 ml of 2.5 mg per milliliter of avidin was added in PBS (0.05 M Na$_2$HPO$_4$, 0.15 M NaCl, pH=7.4), and after incubation at 23° C., 2 ml of cold 0.025% neutral-dextran 80 (Sigma Chemical Co., St. Louis, Mo.) and 0.25% activated charcoal in Ringers solution (10 mM Hepes, pH=7.4) was added while mixing, incubated 5 minutes at 4° C., and centrifuged at 10,000 g for 5 minutes at 4° C. The supernatant was clarified by filtration through an 0.22μ Millex GV filter (Millipore Corporation, Bedford, Mass.) and stored at −20° C. In the absence of avidin, the labeled DDLVP was entirely depleted by the dextran-coated charcoal separation, but in the presence of avidin, the biotinylated I$^{125}$ DDLVP remained in the final supernatant.

The in vitro studies were performed with isolated bovine brain capillaries used as an in vitro model of blood brain barrier (BBB) transport (16). The findings demonstrated avidin-mediated uptake of biotin, biotinylated peptide, and biotinylated antisense oligonucleotide by isolated bovine brain capillaries in-vitro.

In particular, it was found that brain capillary preparations preferably took up [H$^3$]-biotin, [I$^{125}$]-bio-SS-DDLVP, or [P$^{32}$]-bio-DNA coupled to avidin whereas minimal uptake was observed without the avidin transport vector.

A control study indicated that the uptake of the biotin is approximately 4-fold greater than the uptake of avidin, consistent with 4 biotin binding sites per avidin tetramer (13).

The brain capillary uptake of [H$^3$]-biotin was found to be negligible in the presence of buffer (Ringer's buffer, 10 mM Hepes Buffer, pH=7.4) alone. However, when avidin was added to incubation, the brain capillaries avidly took up [H$^3$]-biotin. In contrast, the addition of 500 nM of streptavidin to the incubation mixture resulted in no increased uptake of the biotin. In this Example, streptavidin acted as an important control. This bacterial homologue of avidin is 38% homologous with avidin (26), has a similar size and molecular structure, but differs from avidin by having a slightly acidic pI of 5 to 6 (15).

The differences between the cationic avidin and the slightly acidic streptavidin underscored the importance of the cationic nature of avidin, which initiated the absorptive-mediated endocytosis of the avidin-biotin complex by brain capillaries.

Similar to other cationic proteins, such as cationized albumin or histone (16, 17), the absorptive-mediated endocytosis of avidin by isolated brain capillaries is competitively inhibited by the polycationic protein, salmon protamine (Sigma grade 4), with a Ki=5 μg per ml protamine (data not shown).

Another finding indicated that uptake was mediated by the cationic nature of avidin, not the attached carbohydrate. 50 mM α-methylmannoside (αMM) resulted in no significant inhibition of the uptake of the avidin-biotin complex by brain capillaries in vitro. These findings showed that the mannose-rich carbohydrate moiety of avidin does not trigger the saturable uptake of avidin by isolated brain capillaries (27).

The uptake by brain capillaries of [I$^{125}$]-bio-SS-DDLVP (0.5 μCi/ml, specific activity=190 μCi/μg) was found to be negligible in the presence of Ringer's buffer, but was markedly increased in the presence of 500 nM avidin. In contrast, the pretreatment of the [I$^{125}$]-bio-SS-DDLVP-avidin complex with dithiothreitol (DTT) prior to addition to the isolated brain capillary brain preparation resulted in a marked decrease in the capillary uptake of the (I$^{125}$)-DDLVP peptide. The decreased uptake caused by the DTT treatment was due to cleavage of the disulphide bond, which separated the biotinylated DDLVP peptide from the avidin vector, as in Formula II, below.

Formula II

The uptake of [P$^{32}$]-bio-antisense oligonucleotide by isolated brain capillaries was relatively low and the uptake was greatly increased by the addition of 800 nM avidin to the incubation mixture. Conversely, there was no significant increase in uptake when 800 nM streptavidin was added to the incubation mixture.

The modest uptake of radioactivity in the presence of buffer alone represents uptake of [P$^{32}$] nucleotide or phosphate ion generated by capillary nuclease or phosphatase degradation of the antisense oligonucleotide. All incubations were performed at 23° C. for thirty minutes with brain capillary (about 100 μg protein per flask).

In Vivo

To demonstrate in vivo uptake, [H$^3$]-biotin/unlabeled streptavidin and [I$^{125}$]-avidin were co-injected intravenously into anaesthetized male Sprague-Dawley rats (250–300 grams) and serum radioactivity was measured for up to two hours after injection as DPM/ml as a percent of injected dose (17).

The [H3] biotin radioactivity data was fit to a monoexponential decay function using a non linear regression analysis to yield the intercept and slope (K) of the clearance curve. The half-time of clearance was calculated from K. The serum trichloroacetic acid (TCA) precipitable [I$^{125}$]-avidin radioactivity data was fit to a biexponential clearance function as described previously (17). The intercepts and slopes of the clearance curves were used to compute the integral of serum radioactivity at each respective time point, and these integrals were used to calculate the volume of distribution ($V_D$) values (17). For other findings, [H$^3$]-biotin was similarly co-injected with an excess of unlabeled avidin and organ $V_D$ values were computed.

Another in vivo example was performed in a parallel fashion to the in vitro study reported above. The findings demonstrated the avidin-mediated tissue uptake of [H$^3$]-biotin, avidin-mediated tissue uptake of [I$^{125}$]-bio-SS-DDLVP, and enhanced in vivo avidin-mediated tissue uptake of [P$^{32}$]-bio-antisense oligonucleotide.

Groups of rats were administered [H$^3$]-biotin along with unlabeled streptavidin and [I$^{125}$]-avidin and the rate of clearance of [H$^3$]-biotin or the [I$^{125}$]-avidin from serum was measured over a two-hour period. The [H$^3$]-biotin coupled to an excess of streptavidin was cleared relatively slowly with a half time of 2.4±0.2 hours. Conversely, the [I$^{125}$]-avidin was cleared rapidly in a biexponential mechanism characterized by half times of 22±13 seconds and 53±6 minutes. In other experiments, [H$^3$]-biotin was injected with excess quantities of unlabeled avidin and the rate of clearance of the [H$^3$]-biotin from blood in these experiments paralleled that for the [I$^{125}$]-avidin.

In these studies, [H$^3$]-biotin/unlabeled streptavidin and [I$^{125}$]-avidin were intravenously co-injected into anesthetized male Sprague-Dawlely rats (250–300 g) and serum radioactivity was measured for up to 2 hours after injection as DPM/ml as a percent of injected dose (29). The [H$^3$]-biotin radioactivity was fit to a monoexponential decay function using a non-linear regression analysis to yield the intercept and slope of the clearance curve. The half-time was calculated from ln2/slope of the clearance curve. The serum trichloroacetic (TCA) precipitable [I$^{125}$]-avidin radioactivity data was fit to a biexponential clearance function (29) to yield the intercepts and slopes of the two components of clearance. The intercepts and slopes of the clearance curves were used to compute the integral of serum radioactivity at each respective time point, and these integrals were used to calculate the volume of distribution, $V_D$.

The integrals of the plasma radioactivity for either the experiments involving the injection of [H$^3$]-biotin-streptavidin or [H$^3$]-biotin-avidin were computed from a pharmaco-kinetic analysis (17) of the findings. These integrals of plasma radioactivity were used to compute the organ volume of distribution ($V_D$) of H$^3$-biotin in brain, liver, kidney, heart, and lung.

The findings demonstrated that the rapid clearance of the avidin-biotin complex from blood was due to uptake by liver and kidney, and that 10–20 times more biotin was delivered to the liver and kidney at 5 minutes after a single intravenous injection when the [H$^3$]-biotin was co-injected with avidin, as compared to the streptavidin co-injection.

The liver and kidney biotin $V_D$ rose to values 100- to 200-fold higher when biotin was co-injected with avidin as compared to streptavidin by two hours after injection. By that time, the $V_D$ of the [H$^3$]-biotin in brain following co-injection with avidin was more than five-fold greater than the $V_D$ value observed when [H$^3$]-biotin was co-injected with streptavidin.

The calculations for the above findings involved plotting the ratio of the [H$^3$]-biotin organ $V_D$ value after co-injection with avidin relative to the [H$^3$]-biotin organ $V_D$ value following co-injection with streptavidin versus time after a single intravenous injection of the isotope in anesthetized rats. The findings indicated that avidin selectively delivered biotin to liver and kidney and, to a lesser extent, brain and heart relative to streptavidin as a vector.

The liver $V_D$ value for a plasma marker, [H$^3$] rat serum albumin (RSA), for [I$^{125}$]-bio-SS-DDLVP co-injected with an excess of avidin, and for [I$^{125}$]-bio-SS-DDLVP co-injected with an excess of avidin following a thirty minute incubation with 25 mM dithiothreitol (DTT) were calculated. In the study leading to these calculations, the tail artery of the anesthetized rats was cannulated with PE-50 tubing and approximately 1 ml of arterial blood was collected over the five minute period following a rapid intravenous injection of isotope. The liver $V_D$ value was computed by dividing the tissue radioactivity (DPM/g) by the integrated arterial serum radioactivity (DPM/ml). Thus, this external organ technique allowed for computation of organ $V_D$ values using the integral of serum radioactivity obtained experimentally and was suitable for short timed experiments.

The serum radioactivity obtained five minutes after injection of [I$^{125}$]-bio-SS-DDLVP co-injected with avidin was applied to a Superose 12-HR fast protein liquid chromatography (FPLC) column, and the majority of the radioactivity eluted at 12 ml, which was identical to the elution volume of the (I$^{125}$-avidin control. In contrast, the biotinylated [I$^{125}$]-DDLVP standard eluted at 16 ml. These data demonstrated that the majority of the biotinylated peptide was intact and bound to avidin during the experimental circulation.

The findings also demonstrated the marked increase in liver volume of distribution of [I$^{125}$]-bio-SS-DDLVP when the molecule was co-injected with avidin. For example, the 5-minute $V_D$ of the DDLVP-avidin complex was more than seven-fold greater than the $V_D$ of the co-injected [H$^3$]-rat serum albumin (RSA). The RSA distributes into the plasma space of the liver and represents the organ $V_D$ value expected if there was no cellular uptake of the injected drug. RSA and avidin have essentially the same molecular weight (13). Therefore, the $V_D$ value of RSA and DDLVP coupled to avidin should be identical in the absence of specific cellular uptake of the avidin complex. Conversely, when the [I$^{125}$]-bio-SS-DDLVP was treated with dithiothreitol (DTT) for 30 minutes prior to intravenous injection, the hepatic $V_D$ decreased by more than two-thirds relative to the hepatic $V_D$ values observed when there was no disulphide cleavage of the biotinylated DDLVP from the avidin vector.

In other studies, rat serum obtained two hours after an intravenous injection of [H$^3$]-biotin and streptavidin was eluted through the Superose 12-HR FPLC column and all [H$^3$]-radioactivity co-migrated with streptavidin, not free biotin. These studies reaffirmed previous demonstrations of the stability of the avidin-biotin bond in the circulation (18, 25).

The liver and kidney $V_D$ values were determined with the external organ technique for a plasma marker [H3]-RSA, for

[P³²]-bio-DNA co-injected with avidin, and for [P³²]-bio-DNA co-injected with streptavidin. The data demonstrated that avidin selectively delivered the antisense oligonucleotide to liver and kidney in vivo, whereas streptavidin resulted in a distribution of the antisense oligonucleotide to these organs that is no greater than that of the RSA plasma marker, which has a molecular weight comparable to that of avidin. Serum obtained from these rats at the end of the circulation period was analyzed with a dextran-coated charcoal separation technique, which showed that more than 95% of the [P³²]-bio-DNA was bound by avidin in the circulation.

The liver and kidney $V_D$ values for [H³]-RSA or [P³²]-bio-antisense DNA co-injected with either avidin or streptavidin were determined. In both organs, the $V_D$ value for the [P³²]-bio-antisense-DNA co-injected with either avidin or streptavidin were determined. In both organs, the $V_D$ value for the [P32]-bio-antisense-DNA co-injected with streptavidin was comparable to the $V_D$ value of the plasma marker, [H³]-RSA. Conversely, there was a five- to ten-fold increased tissue uptake of the [P³²]-bio-antisense DNA following co-injection with avidin.

EXAMPLE 2
Polycationic Protein Inhibition of Avidin Vector Uptake

This study was performed to demonstrate inhibition of uptake of the avidin-biotin complex by isolated bovine brain capillaries caused by increasing concentrations of another polycationic protein, protamine. For this study, isolated brain capillaries were incubated with trace amounts of [H³]-biotin that was stoichiometrically bound to 1 mg per ml medium avidin, and the uptake was inhibited 50% by 5 µg per ml of protamine. The findings demonstrated that the absorptive-mediated endocytosis of the avidin-biotin complex by isolated bovine brain capillaries was a function of the polycationic nature of the avidin protein (16).

In other studies, the uptake of the avidin-biotin complex by isolated brain capillaries, used as an in vitro model system of blood-brain barrier transport, was shown to be time-dependent, temperature-dependent, and that the uptake was approximately 50% resistant to a mild acid wash assay used as a measurement of absorptive mediated endocytosis (16).

EXAMPLE 3
Avidin Protection of Biotinylated Antisense Oligonucleotide Against Degradation by Serum Exonuclease The invention provides a method for protecting biotinylated antisense oligonucleotides from serum exonuclease degradation. The steps of this method are demonstrated in this example. The protocol and results are presented in FIGS. 1a, 1b, and 1c.

Figure 1A:
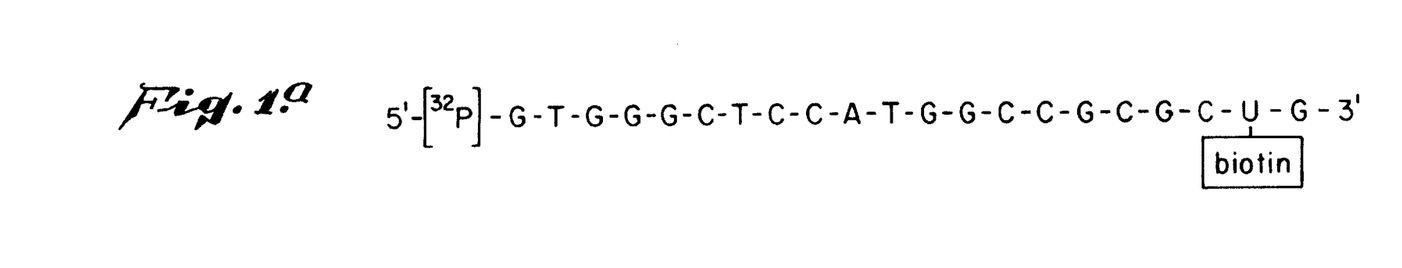
FIG. 1a shows a 21-mer antisense oligonucleotide with a biotin placed toward the 3' end.

FIG. 1a shows a 21-mer antisense oligonucleotide complementary to nucleotides 160–181 of the bovine GLUT-1 glucose transporter mRNA. This 21-mer was synthesized with an extended primary amine group by replacement of the deoxythymidine at position 20 with 6-amino-deoxyuridine, biotinylated with NHS-biotin and purified by the manufacturer (Genosys Biotechnologies, Inc., The Woodland, Tex.). The oligonucleotide was labelled at the 5' end with [γ-P³²]-ATP using $T_4$ polynucleotide kinase to a specific activity of 1.1 microcuries/pmol. The labeled product was purified through Sephadex G-25 column. An aliquot of 12.8 pmol [P³²]-oligonucleotide was incubated with 140 µg avidin in 100 µl PBST (PBST=10 millimolar phosphate buffer, pH 7.5; 0.15 M NaCl; 0.1% bovine serum albumin; 500 µg tRNA/ml) at room temperature for 15 minutes. The avidin-[P³²]-oligonucleotide complex was purified by Sephadex G-75 column, prior to the experiment.

Figure 1B:
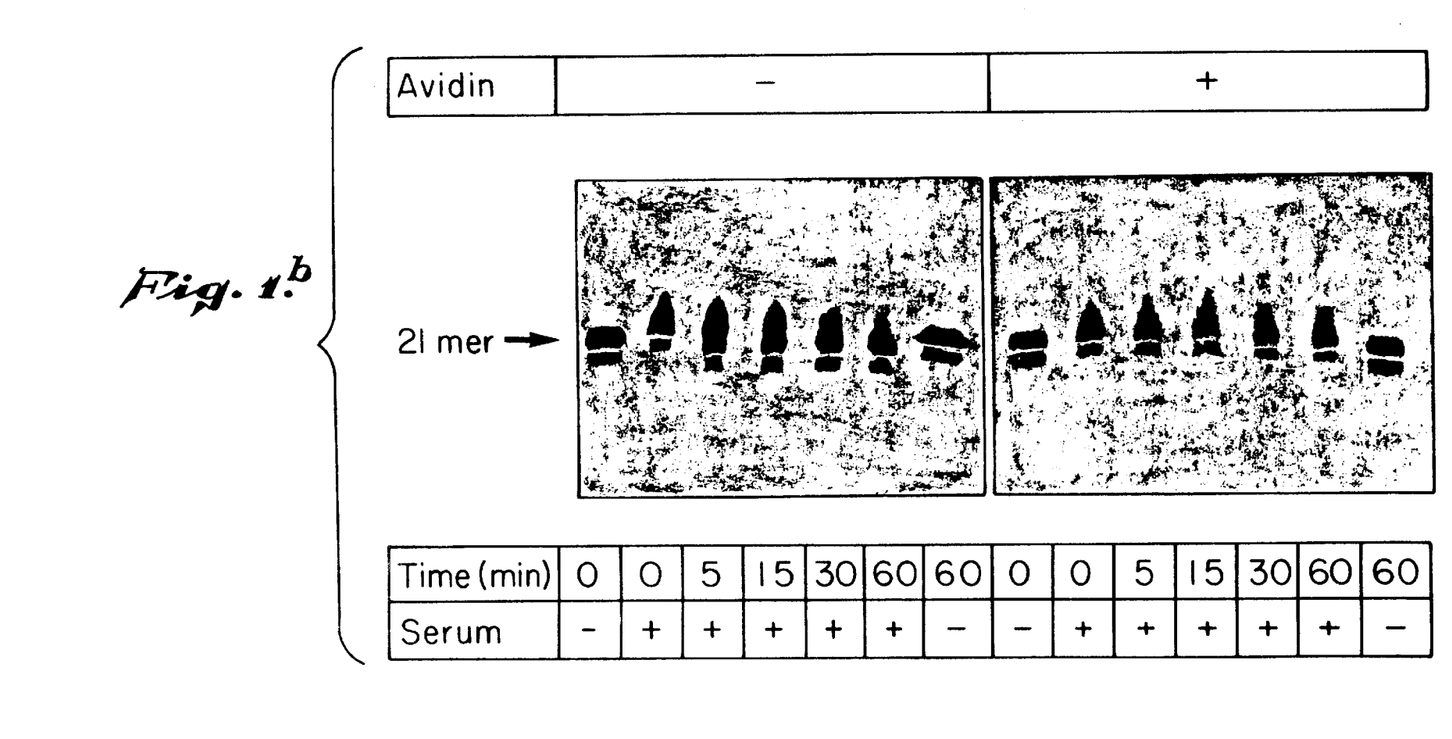
FIG. 1b shows an autoradiogram of a gel demonstrating avidin's prolonging effect on the stability of biotinylated oligonucleotides in serum.

FIG. 1b shows the effect of avidin on the stability of biotinylated oligonucleotide in serum. In this aspect of the study, 4 µl PBST containing 6 fmol [P³²]-oligonucleotide or [P³²]-oligonucleotide-avidin complex were incubated with PBST or rat serum (16 µl) at 37° C. for the time indicated in the Figure. The reaction was stopped by transferring tubes onto an ice bath and adding two volumes of 8 M urea-10% glycerol. Samples were heated 5 minutes at 95° C. and incubated 5 minutes on ice immediately before resolving them in a 15% polyacrylamide-7 M urea sequencing gel. The autoradiogram of the gel is shown in FIG. 1b.

Figure 1C:
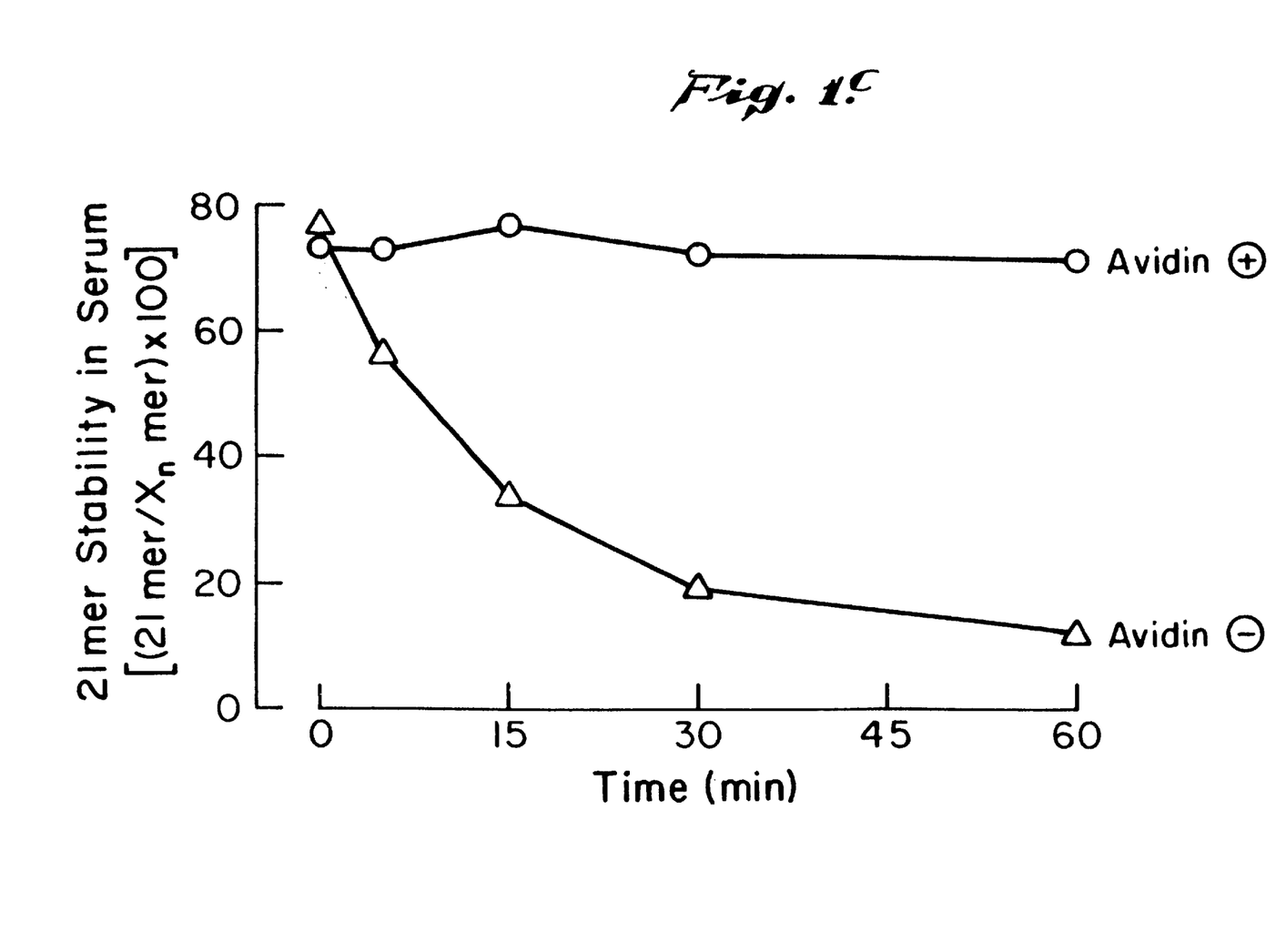
FIG. 1c, shows a quantitation of the autoradiogram of portion FIG. 1b indicating avidin protecting the biotinylated oligonucleotide against degradation by 3' exonuclease in serum.

FIG. 1c shows a quantitation of the autoradiogram by laser scanning densitometry (LKB Model 2202 Ultrascan Laser Densitometer Bromma, Sweden). The results are expressed as percent 21-mer [P³²]-oligonucleotide $X_n$ [P³²]-oligonucleotides (degradation products). The labelled oligonucleotide is 80% 21-mer and 20% 20-mer [P³²]-oligonucleotide. Incubation of the unprotected (avidin-) [P³²]-oligonucleotide with serum (triangles) showed a rapid conversion to degradation products (20- and 19-mer) with a half-life (t½) of approximately 13 minutes. On the other hand, incubation with avidin (avidin+) totally protected the [P³²]-oligonucleotide against degradation by the 3' exonuclease in serum during the incubation period.

EXAMPLE 4
Avidin Fusion Protein Vector

This experiment was performed to demonstrate that avidin may be fused to a tissue-specific targeting moiety to form a tissue-specific transport vector comprising an avidin fusion protein. Such fusions can be achieved chemically, as in this example, or can be achieved genetically, as shown in FIG. 2.

The avidin fusion protein tissue-specific transport vector allows for specific targeting of any biotinylated peptide, drug, or antisense oligonucleotide. Furthermore, complex linker chemistry is eliminated by the method of the present invention for synthesizing avidin-fusion proteins comprising tissue-specific transport vectors.

In previous studies (29), cationized rat serum albumin has been shown to be a semi-brain specific transport vector, and to undergo absorptive-mediated endocytosis at brain capillaries in vitro and absorptive-mediated transcytosis across brain capillaries in vivo (29). The use of cationized rat albumin as a brain transport vector would normally necessitate complex linker chemistry involving the attachment of each individual drug to the cationized rat albumin transport vector. The method of the present invention, however, no longer requires complex linker chemistry to link cationized rat albumin to multiple drugs. The method of the present invention simply requires biotinylation of the various drugs that may be coupled to the avidin fusion protein for drug delivery to the brain.

In this example, the uptake of [H³] by isolated bovine brain capillaries was shown to be nil in the presence of Ringer Hepes buffer or in the presence of buffer containing cationized rat albumin at a concentration of 150 nM. However, the uptake of the [H³] biotin was greatly facilitated by the addition of a cationized rat albumin/avidin conjugate at a concentration of 15 nM.

In other work, the uptake by isolated bovine brain capillaries of [P³²] biotinylated antisense oligonucleotide was measured after a 30 minute incubation of the isotope at either 4° C. or 37° C. in the presence of Ringer-Hepes buffer alone, cationized rat albumin (15 nM), or a cationized rat albumin/avidin conjugate (2.4 nM). The data was collected to reflect triplicate trials. The experiments showed that cationized rat albumin alone did not facilitate the uptake of the [P$^{32}$] biotinylated antisense oligonucleotide, but that the cationized rat albumin/avidin fusion protein did mediate the uptake of the biotinlyated antisense oligonucleotide by brain capillaries, and that this process was impaired by incubation at low temperatures, consistent with absorptive-mediated endocytosis.

In this example, the cationized rat albumin/avidin fusion protein was prepared by coupling avidin to thiolated cationized rat albumin using m-maleimidobenzoyl-N-hydroxysuccinimide ester (MBS). The cationized rat albumin was thiolated with N-succinimidyl S-acetylthioacetate (SATA) and hydroxylamine. The MBS and SATA are standard coupling reagents and were purchased from Pierce Chemical Company, Rockford, Ill.

Examples 1–4 provided in vivo and in vitro demonstrations that avidin-biotin technology of the present invention are appropriately applied to blood-brain barrier delivery of antisense oligonucleotides and peptides. In addition, the avidin-biotin technology of the present invention may also be employed to deliver antisense oligonucleotides or peptide pharmaceuticals to peripheral tissues, such as liver or kidney.

Although the present invention has been described in considerable detail with regard to certain preferred versions, other versions are possible. For example:

Vasopressin analogues are believed to be possible treatments for amnesia, but the successful use of these peptides in treatment of neurologic disorders has been limited by the poor transport of vasopressin across the blood-brain barrier. The DDLVP delivery to the brain using the avidin biotin technology described in Example 1 and 2 above may be used to transport the peptide across the blood-brain barrier. Alternatively, an avidin fusion protein, such as described in Example 4, above, may be used to transport DDLVP to brain, wherein the avidin fusion protein is comprised of avidin joined to a brain-specific transport vector.

Further, the antisense oligonucleotide used in Examples 1 and 2 above corresponds to the sequence flanking the methionine initiation codon of the GLUT-1 glucose transporter isoform mRNA. This gene is overexpressed in malignant tissues (28). The delivery of the antisense oligonucleotide to liver or kidney cancer using the compositions of the present invention may impair the production of the glucose transporter in the cancer cell, thus starving the malignant cell of the glucose energy source, resulting in malignant cell necrosis.

The present invention is also useful for delivery of antisense oligonucleotides to cultured cells in vitro in scaled up industrial level production of recombinant proteins. The composition of the invention can deliver to these cells antisense oligonucleotides that impair the production of proteases that degrade the recombinant protein being expressed in the transfected cultured cell. This would increase yield of the recombinant protein, e.g., insulin, and enhance industrial expression system by impairing the degradation of the recombinant protein.

In still another example, an antisense oligonucleotide selected for a viral-specific mRNA may be delivered to tissues using this technology for the purposes of treatment of the viral disease. Similarly, the delivery of an antisense oligonucleotide selected for a tumor-specific oncogene may be delivered for the treatment of a cancer. Similarly, a sense oligonucleotide that binds a cytosolic mRNA stability factor may be delivered to tissues for the purpose of increasing the degradation of tumor-specific mRNA.

The avidin-biotin technology may also be used in the diagnosis of disorders using standard imaging technology such as positron emission tomography or single photon computer emission tomography. For example, a radio-labelled cholecystokinin (CCK) peptide may be delivered to brain using the present invention for the purpose of imaging CCK-specific receptors in the diagnosis of mental disorders. Conversely, a radio-labeled antisense oligonucleotide may be delivered to tissues for the purpose of imaging cancer or viral disorders.

The spirit and scope of the appended claims should not be limited to the description of the preferred versions contained therein.

BIBLIOGRAPHY

1. H. Weintraub, J. G. Izant, R. M. Harland, *Trends in Genetics*, Vol. 1, pp. 23–25, 1985; C. A. Stein, J. S. Cohen, *Cancer Research*, Vol. 48, pp. 2659–2668, 1988.
2. R. J. Boado, W. M. Pardridge, *Molec. Cell. Neurosci.*, Vol. 1, pp. 224–232, 1990.
3. S. L. Loke, C. A. Stein, X. H. Zhang, K. Mori, M. Nakanishi, C. Subasinghe, J. S. Cohen, L. M. Neckers, *Proc. Natl. Acad. Sci. U.S.A.*, Vol. 86, pp. 3474–3478, 1989; J. A. M. Maier, P. Voulalas, D. Roeder, T. Maciag, *Science*, Vol. 249, pp. 1570–1574, 1990; J-P. Leonetti, P. Machy, G. Degols, B. Lebleu, L. Leserman, *Proc. Natl. Acad. of Science. U.S.A.*, Vol. 87, pp. 2448–2451, 1990.
4. M. Matsukura, K. Shinozuka, G. Zon, H. Mitsuya, M. Reitz, *Proc. Natl. Acad. Sci. U.S.A.*, Vol. 84, pp. 7706–7710, 1987.
5. Malone, R. W., Felgner, P. L., and Verma, I. M., *Proc. Natl. Acad. Sci. U.S.A.*, Vol. 86, pp. 6077–6081, 1989.
6. Gregoriadis, G., *New England Journal of Medicine*, Vol. 295, pp. 704–710, 1976.
7. W. M. Pardridge, *Endocrine Review*, Vol. 7, pp. 314–330, 1986.
8. G. Y. Wu, C. H. Wu, *Journal of Biological Chemistry*, Vol. 263, pp. 14621–14624, 1988.
9. E. Wagner, M. Zenke, M. Cotten, H. Beug, M. L. Birnstiel, *Proc. Natl. Acad. Sci. U.S.A.*, Vol. 87, pp. 3410–3414, 1990.
10. Th. J. Postmes, M. Hukkelhoven, E. J. M. van den Bogaard, S. G. Halders, J. Coenegracht, *Journal of Pharm. Pharmacol.*, Vol. 32, pp. 722–724, 1980.
11. W. M. Pardridge, D. Triguero, J. L. Buciak, *Endocrinology*, Vol. 26, pp. 977–984, 1990.
12. M. Lemaitre, B. Bayard, B. Lebleu, *Proc. Natl. Acad. Sci. U.S.A.*, Vol. 84, pp. 648–652, 1987.
13. N. M. Green, *Advances in Protein Chemistry*, Vol. 29, pp. 85–133, 1975.
14. Korpela, J., *Med. Biol.*, Vol. 62, pp. 5–26, 1984.
15. N. M. Green, *Methods in Enzymology*, Vol. 184, pp. 51–67, 1990.
16. A. K. Kumagai, J. Eisenberg, W. M. Pardridge, *Journal of Biological Chemistry*, Vol. 262, pp. 15214–15219, 1987.
17. W. N. Pardridge, D. Triguero, J. B. Buciak, *Journal of Pharmacology and Exp. Ther.*, Vol. 251, pp. 821–826, 1989.
18. R. D. Wei, D. H. Kou, S. L. Hoo, *Experientia*, Vol. 27, pp. 366–368, 1970.
19. I. I. Kaplan, *American Journal of Medical Science*, Vol. 207, pp. 733–743, 1944
20. M. L. Gope, R. A. Keinänen, P. A. Kristo, O. M. Conneely, W. G. Beattie, T. Zarucki-Schultz, B. W. O'Malley, M. S. Kulomaa, *Nucleic Acids Research*, Vol. 15., pp. 3595–3606, 1987.

21. M. Shimkus, J. Levy, T. Herman, *Proc. Natl. Acad. Sci. U.S.A.*, Vol. 82, pp. 2593–2597, 1985.
22. J. E. Cronan, Jr., *Journal of Biological Chemistry*, Vol. 265, pp. 10327–10333, 1990.
23. Y. Hiller, J. M. Gershoni, E. A. Bayer, M. Wilchek, *Biochemical Journal*, Vol. 248, pp. 167–171, 1987.
24. Capon, D. J. et al., *Nature*, Vol. 337, pp. 525–531, 1989.
25. D. J. Hnatowich, F. Virzi, M. Rusckowski, *Journal of Nuclear Medicine*, Vol. 28, pp. 1294–1302, 1987.
26. Gitlin, G., Bayer, E. A., and Wilchek, M., *Biochemical Journal*, Vol. 269, pp. 527–530, 1990.
27. R. C. Duhamel, J. S. Whitehead, *Methods in Enzymology*, Vol. 184, pp. 201–207, 1990.
28. J. S. Flier, M. M. Mueckler, P. Usher, H. F. Lodish, *Science*, Vol. 235, pp. 1492–1498, 1987.
29. W. M. Pardridge, D. Triguero, J. B. Buciak, J. Yang, *Journal of Pharmacol. Exp. Ther.*, Vol. 255, pp. 893–899, 1990.

What is claimed is:

1. A composition for delivery of an agent to cells, said composition consisting of:

a transport vector comprising an avidin moiety;

at least one monobiotinylated agent bonded to said avidin moiety via an avidin-biotin linkage to provide an avidin-biotin-agent complex; and a pharmaceutically acceptable carrier.

2. The composition of claim 1 wherein the monobiotinylated agent comprises a pharmaceutical compound selected from the group consisting of monobiotinylated peptides, antisense oligonucleotides, immunoglobulins, and organic chemicals.

3. The composition of claim 1 wherein the monobiotinylated agent comprises a diagnostic compound selected from the group consisting of monobiotinylated immunoglobulins, oligonucleotides, amyloid ligands, and receptor ligands.

4. The composition of claim 1 wherein the monobiotinylated agent is selected from the group consisting of monobiotinylated oligonucleotides, polypeptides, immunoglobulins, and organic chemicals.

* * * * *